United States Patent [19]

Verstegen et al.

[11] 3,957,868
[45] May 18, 1976

[54] PROCESS FOR PREPARING UREA FROM AMMONIA AND CARBON DIOXIDE

[75] Inventors: Johannes D. M. Verstegen; Petrus J. C. Kaasenbrood, both of Sittard, Netherlands

[73] Assignee: Stamicarbon, B.V., Geleen, Netherlands

[22] Filed: May 16, 1974

[21] Appl. No.: 470,663

[30] Foreign Application Priority Data
May 21, 1973 Netherlands.................. 7307036

[52] U.S. Cl............................................ 260/555 A
[51] Int. Cl.².................................. C07C 126/00
[58] Field of Search..................... 260/555 A, 555 R

[56] References Cited
UNITED STATES PATENTS

| | | | |
|---|---|---|---|
| 3,090,811 | 5/1963 | Otsuka et al. | 260/555 A |
| 3,356,723 | 12/1967 | Kaasenbrood | 260/555 A |
| 3,406,201 | 10/1968 | Baumann et al. | 260/555 A |
| 3,579,636 | 5/1971 | Mavrovic | 260/555 A |
| 3,691,729 | 9/1972 | DeRoey et al. | 260/555 A |
| 3,816,528 | 6/1974 | Cook | 260/555 A |

FOREIGN PATENTS OR APPLICATIONS

| | | | |
|---|---|---|---|
| 1,560,985 | 3/1969 | France | 260/555 R |
| 1,097,974 | 6/1961 | Germany | 260/555 R |
| 952,764 | 7/1964 | United Kingdom | 260/555 R |

*Primary Examiner*—Oscar R. Vertiz
*Assistant Examiner*—Eugene T. Wheelock
*Attorney, Agent, or Firm*—Cushman, Darby & Cushman

[57] ABSTRACT

An improved urea synthesis process is disclosed in which carbon dioxide and ammonia are reacted at 210° to 245°C under pressures of 250 to 600 atm., the gross molar $NH_3/CO_2$ ratio in the liquid phase in the synthesis zone of the order of 2.5 and 8, the carbon dioxide and ammonia being reacted together in a synthesis zone then the resulting urea synthesis solution being stripped in a stripping zone which is in heat exchange relation with the synthesis zone through a wall, and the gas mixture resulting from the stripping is partially recycled to the synthesis zone.

6 Claims, 1 Drawing Figure

U.S. Patent   May 18, 1976   3,957,868
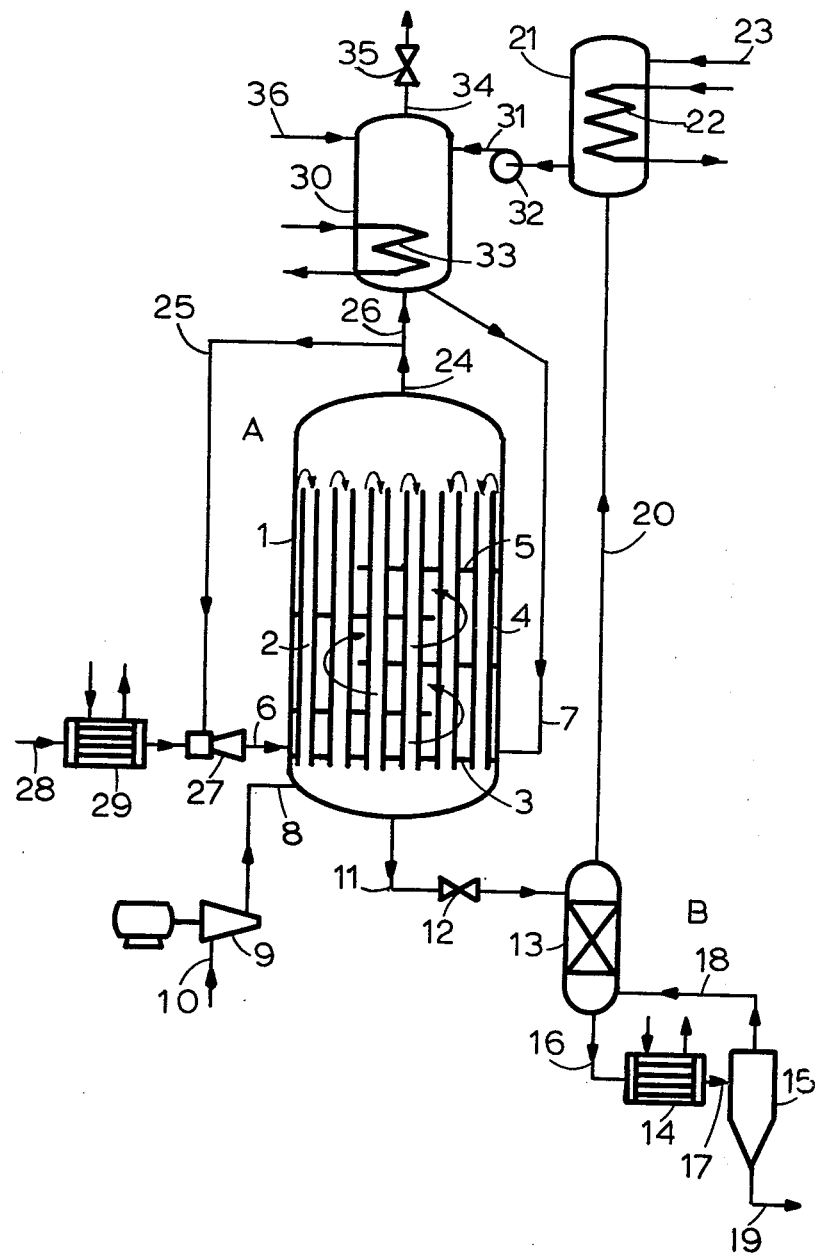

3,957,868

PROCESS FOR PREPARING UREA FROM AMMONIA AND CARBON DIOXIDE

BACKGROUND OF THE INVENTION

This invention relates to an improvement in the process for preparing urea, in which ammonia and carbon dioxide are reacted in a reaction zone and in which, subsequently, in a stripping zone which is in a heat-exchange relationship with the reaction zone through a wall, at a pressure which is substantially equal to that in the reaction zone, ammonium carbamate present in the synthesis solution thus formed is decomposed, the decomposition products are expelled with the aid of gaseous carbon dioxide, ammonia, inert gas or a mixture of at least two of said substances, and urea is produced.

More specifically, the present process represents an improvement on the basic process described in U.S. Pat. No. 3,356,723 to Kaasenbrood, one of the co-inventors herein, and, more recently to U.S. Pat. No. 3,406,201 to Baumann et al. The disclosures of these patents are hereby incorporated by reference to the extent necessary to understand and further explain the process described herein.

A process of this general type has already been desribed in U.S. Pat. No. 3,406,201 which indicates a "heat integrated reactor-decomposer" system using a stripping treatment using the heat liberated during the formation of ammonium carbamate, to which end the reaction zone is located at the outside of the heat-exchange tubes in which the stripping takes place. Applicants have observed that the manner in which the carbamate is formed in such a reaction zone to a practical degree is not fully explained, for the ammonia introduced into the bottom part of the reaction zone and is only contacted with the gaseous carbon dioxide required for the formation of carbamate and urea in the gas chamber above the tubes. This is because the carbon dioxide is first used as stripping gas in the tubes and, subsequently, after being mixed with expelled carbon dioxide, ammonia and water, flows out of the tubes at the top. Another disadvantage to this known process is that at the temperatures and pressures given, the carbamate present in the synthesis solution can only be decomposed to a sufficient extent in the stripping zone by adding heat to the system from an outside source.

DETAILED DESCRIPTION OF THE INVENTION

An object of the invention is to provide an improved process in which these problems are obviated and urea produced in substantially higher yields in a more compact apparatus without resort to external heating means. The process according to the invention is characterized in that: (a) temperatures of 210° to 245°C. are preferably 215°–230°C. are maintained in the reaction zone; (b) a pressure of 250 to 600 atm. is maintained in the reaction zone; (c) the gross molar $NH_3/CO_2$ ratio in the liquid phase in the reaction zone is between about 2.5 and about 8; and (d) at least part of the gas mixture discharged from the stripping zone is introduced into the bottom part of the reaction zone. The term gross molar $NH_3/CO_2$ ratio is used herein refers to the ratio of ammonia to carbon dioxide including both the free and chemically bound forms thereof.

If, as is the case of the process according to the present invention, ammonia and carbon dioxide are reacted at a substantially higher temperature and pressure than those previously used, a certainly smaller portion of the reactants is converted into ammonium carbamate, but a larger portion of the intermediate product is converted into urea. Further, under these conditions, the evaporation heat values of the ammonia and carbon dioxide contained in the urea synthesis solution are smaller. Therefore, in the stripping zone a smaller amount of heat will be sufficient, because less ammonium carbamate is decomposed and because the amount of heat necessary to expel the dissolved ammonia and carbon dioxide from the synthesis solution is smaller.

In the process according to the present invention a two-phase flow is maintained in the reaction zone, and owing to this flow a more intensive heat transfer takes place from the reaction zone to the stripping zone. In this way it is possible for the amount of heat required for the stripping treatment — which heat quantity, because of the smaller amount of carbamate and the lower evaporation heat values of ammonia and carbon dioxide, is smaller than is the case with the previously used temperature and pressure conditions — to be transferred to the synthesis solution to be stripped via a relatively small heat-exchange surface area. In the process according to the present invention no heat need be supplied from a source external to the synthesis solution to be stripped. Another advantage is that the process may be carried out in an installation of compact design, with a heat-exchange surface on either side of which equal pressures prevail.

For optimum heat transfer it is preferable that, per unit of time, a quantity of gas mixture be returned or recycled to the reaction zone which is larger than the sum of (a) the quantity of inert gases supplied per time unit to the reaction zone with the reaction components and (b) the quantity of gas mixture discharged per unit of time out of the stripping zone. To this end, according to the present invention, we prefer to use a gas mixture which consists of unconverted ammonia and carbon dioxide and inert gases being discharged at the top of the reaction zone, and to a quantity thereof, corresponding with 10 to 50 percent by weight of the gas mixture discharged from the stripping zone, being reintroduced into the reaction zone at a lower level.

It is no necessary here for the gas mixture from the stripping zone and for the gas mixtur itself to be recycled from the reaction zone to be separately reintroduced into the bottom part of the reaction zone. By preference, the two mixtures are jointly, if necessary at different levels, directed into the reaction zone, for instance from a common collecting-chamber above the reaction zone and the stripping zone. An ejector driven by means of ammonia, carbon dioxide or a solution containing ammonium carbamate is particularly well suited for this arrangement.

The present invention will be further elucidated and illustrated in the attached schematic FIGURE.

The combined reactor-stripper unit, indicated by A and shown in cross-section, consists of a vertically arranged cylindrical vessel 1, in which a number of tubes 2 are installed, also in vertical position. The lower ends of the tubes 2 are fixed in the tubesheet 3. The shell chamber 4 surrounding the tubes 2 is in open connection, at the top, with the internal space of the tubes as there is no sealing upper tubesheet. If necessary, staggered horizontal baffles 5 may be installed in the shell chamber 4. To the shell chamber 4 line 6 is connected for the supply of a gaseous reaction mixture and line 7 for the supply of a recirculation solution. The space below the tubesheet 3 is connected via line 8 with carbon dioxide compressor 9, supplied via the line 10 with fresh carbon dioxide and via the line 11, in which reducer valve 12 is installed, with the low-pressure stage B. The low-pressure stage B comprises rectifying column 13, heater 14 and gas-liquid separator 15, which are connected to each other via lines 16, 17 and 18. The gas-liquid separator 15 is connected to liquid discharge line 19, rectifying column 13 being connected, via gas discharge line 20 to condensor 21, which is provided with cooling elements 22 and line 23 for the supply of process liquid.

The space above the tubes 2 in the reactor-stripper unit A is connected with gas discharge line 24 bifurcated into lines 25 and 26. Line 25 runs to ejector 27, which is connected to ammonia line 28, in which an $NH_3$ heater 29 is optionally installed. The significance of heaters 14 and 29 is explained below. Line 26 runs to washing column 30, which, via line 7, is connected to the shell chamber 4 of reactor-stripper unit A and, further, via line 31 and pump 32, to condensor 21. The washing column contains cooling elements 33 and is provided with gas discharge line 34 with reducer valve 35 and, optionally, with line 36 for the supply of ammonia.

Referring now to the arrangement described above, the process according to the present invention is conducted in the following manner: A gas mixture is introduced via line 6, into the bottom part of shell chamber 4 of the reactor-stripper unit A, the chamber acting as the reaction zone, the gas mixture consisting essentially of $NH_3$ and $CO_2$, but also containing water vapor and inert components, while a carbamate solution is introduced through line 7. The temperature in the reaction zone is kept at values of between 210° and 220°C. The gross molar $NH_3/CO_2$ ratio in the gas-liquid mixture in the shell chamber 4, that is the ratio of both the free and the bound $NH_3$ and $CO_2$, is set at, for instance, 3.5. The pressure in the reactor-stripper unit lies, for instance, between 300 and 320 atm. In the shell chamber a portion of the $NH_3$ and the $CO_2$ condenses into carbamate, an amount of heat being liberated. The carbamate thus formed is partly converted by dehydration into urea using part of the liberated heat of the carbamate formation. At the high temperatures and pressures here applied the reaction speed is appreciably higher than under the reaction conditions which have been previously used. The volume of the reaction zone, that is of the shell chamber 4, may accordingly be smaller.

Although formation of carbamate and urea takes place in the gas-liquid mixture, this mixture will, if baffles 5 are present, rise up to the top of the tubes 2, while flowing a number of times virtually horizontally around the tubes, whereupon, in the space above the tubes, the major portion of the gaseous components still present will separate from the synthesis solution. The synthesis solution flows over into the tubes 2 via non-drawn distributor elements causing the solution to flow downwardly in a thin film along the internal wall of the tubes. The falling synthesis solution here flows countercurrently with respect to gaseous $CO_2$ which acts as stripping gas and which has been supplied through the line 8 after having been brought at the required pressure by compressor 9. During this stripping treatment the larger part of the carbamate which has not been converted into urea is decomposed into $NH_3$ and $CO_2$. The heat required for this purpose is supplied exclusively by the gas-liquid mixture in the shell chamber 4; no external heat source is required. For this purpose the part of the carbamate formation heat value not consumed in the conversion of carbamate into urea is available. As previously mentioned, the volume of the reaction zone is conveniently relatively small, but also as a result of this the space available for installation of the heat-exchanging surface is small. Moreover, no heat is supplied from the outside, except, of course, by means of the streams supplied through the lines 6 and 7, and only the surplus heat available in the shell chamber 4 is efficiently used. For these reasons it is necessary to provide for an optimum heat transfer via the walls of the tubes 2 and this object is achieved by directing part of the gas mixture separated off in the space above the stripper tubes 2 (the mixture consisting of unconverted $NH_3$, $CO_2$, $H_2O$ and inert components) into the bottom part of the reaction zone in shell chamber 4 via lines 24 and 25, ejector 27 and line 6. With the aid of this recirculated gas mixture an intensive heat transfer from the gas-liquid mixture to the walls of the tubes 2 is obtained. In order that a sufficient amount of gas mixture be available, in view of an optimum heat transfer, the residence time of the reaction mixture in the shell chamber 4 is adjusted such that not all of the $CO_2$ supplied via the line 6 is converted into carbamate, but rather that part of the $CO_2$ as well as the unconverted $NH_3$, reaches the space above the tubes 2 in the form of a gas. Also the $CO_2$ and $NH_3$ are then returned, in part, to the reaction zone in shell chamber 4.

If required, the ejector 27 can be driven with $CO_2$ or with a recycled carbamate solution. Of course, instead of an ejector a booster compressor may also be used for recirculation of the gas mixture. The amount of gas recirculated influences the heat transport and, as a consequence, the heat balance of the integrated reactor-stripper unit A, the degree of conversion in the reaction zone and the efficiency of the stripping treatment. In view of this it is desirable that the quantity of gas mixture recirculated to the reaction zone via line 25 be controlled with respect to and depending upon the temperature or the composition of the stripped synthesis solution which is discharged through line 11.

That portion of the gas mixture discharged from the space in the top part of the reactor-stripper unit which is not returned to the shell chamber 4 of the reactor-stripper unit A is directed into washing column 30 through line 26 in order to remove the inert gaseous components from the system. Here the $NH_3$ and $CO_2$ present in the gas mixture are recovered through absorption in a dilute carbamate solution, with formation of a carbamate solution of higher concentration, which solution is directed into the bottom part of the shell space 4 of the reactor-stripper unit via the line 7.

The washing column 30 may be arranged at such a level that the solution formed flows into the shell chamber 4 under the influence of the hydrostatic pressure. The use of a carbamate pump, which requires considerable maintenance owing to erosion and corrosion, is not necessary in this case. That part of the gas mixture which is not absorbed and condensed in the washing column 30 and which consists mainly of inert components is discharged via line 34 and reducer valve 35.

At least part of the heat of absorption liberated in the washing column 30 is discharged by means of cooling elements 33 through which cooling water, or a process liquid to be heated and to be subjected to further processing, flows. This heat, however, may also be utilized for production of low-pressure steam, which may then be used elsewhere in the process. In order that a temperature as high as possible be reached in washing column 30, part of the $NH_3$ necessary for the urea synthesis may be introduced into the column in the liquid state via line 36.

The temperature in shell chamber 4 is controlled by a number of factors. For example, the quantity of heat discharged may be controlled by regulating the amount of coolant directed through cooling elements 33. In this way, the temperature in the shell chamber 4 may be influenced and controlled, since part of the heat of absorption which is not discharged via the cooling elements 33 is carried to the shell chamber 4 by the recycled carbamate solution flowing through line 7. This provides another means to control the heat balance in the reactor-stripper unit, which again may be in dependence of the temperature or the composition of the stripped synthesis solution.

It is also possible for the temperature in shell chamber 4 to be controlled by regulating the temperature of the fresh $NH_3$ supplied via the line 6, for instance using heater 29. In this case, however, the controlling range is somewhat limited because large variations in the temperature of the $NH_3$ would affect the performance of the ejector 27. This can, if necessary, be adjusted by directing a controllable part of the $NH_3$, via a by-pass line (not illustrated) around ejector 27, directly into the reaction zone.

The stripped synthesis solution, which still contains minor amounts of carbamate and dissolved $NH_3$, is discharged from the reactor-stripper unit A via line 11 and expanded in the reducer valve 12 until the pressure amounts to 2–5 atm. The expanded solution is directed into the top part of rectifying column 13 of the low-pressure stage B. The gas mixture liberated during the expansion, which consists of $NH_3$, $CO_2$, and $H_2O$, is discharged via line 20 together with the gas also separated off in the low-pressure stage. The remaining urea solution is directed into heater 14 via line 16 to decompose any carbamate still present. The gas mixture thus liberated is separated from the liquid in gas-liquid separator 15 and, via line 18, led into the bottom part of rectifying column 13, in which it ascends countercurrently with the solution to be rectified. From gas-liquid separator 15 and aqueous urea solution is discharged which, at this point, is virtually free from carbamate. This solution is led through line 19 to a final-processing stage, where it is processed into the desired commercial form, such as a concentrated or water-free urea solution, urea crystals or urea prills.

The mixture of gaseous $NH_3$, $CO_2$ and $H_2O$ separated off in low-pressure stage B is led through line 20 into low-pressure carbamate condenser 21, in which a dilute carbamate solution is formed, with supply via line 23 of the aqueous solution to be recirculated from the final-processing stage. The heat of condensation is discharged by means of a coolant flowing through the cooling elements 22. The solution obtained is brought up to the synthesis pressure with the aid of pump 32 and directed via line 31 to washing column 30 to be used as an absorption liquid.

The present invention is not limited to the reaction scheme and apparatus described above which is illustrative of a preferred embodiment. For instance, it is also possible to use a reactor-stripper unit in which parallel plates constitute the heat-transfer elements instead of the tubes. It is also possible to separately collect and recirculate the gases not converted in the reaction zone and the gas mixture discharged from the stripping zone. Other variations will be apparent and appreciated by those skilled in the art.

The invention will be further illustrated in the following Example which is referred to in the accompanying Figure and above description of the process.

EXAMPLE

On the basis of the attached diagram $NH_3$ (23,610 kg/h) was supplied through the line 28 at a pressure of 370 kg/cm$^2$ and a temperature of 40°C. before entrance into ejector 27, in order to produce as the final product 1,000 tons of urea per day (24 hours). The required amount of carbon dioxide, 30,555 kg/h, was compressed by means of compressor 9 to 320 kg/cm$^2$, the pressure at which synthesis of carbamate and urea takes place and directed into the stripping zone. The temperature in the top part of the reactor-stripper unit A was 220°C. A quantity of unconverted gas was discharged from the reaction zone, which quantity amounted to 26 percent by weight of the amount of gas discharged from the stripping zone. In the reaction zone, a net amount of heat $7.5 \times 10^6$ kcal/h was available, which was transferred through the wall of tubes 2 to the synthesis solution flowing downwardly in these tubes, the heat being utilized for decomposition of carbamate and evaporation of $NH_3$ and $CO_2$. No extra heat was supplied. The stripped urea synthesis solution discharged from the reactor-stripper unit A via the line 11 was expanded in the reducer valve 12 until the pressure amounted to 3 kg/cm$^2$.

The compositions of the different material flows are given in the attached table together with the relevant temperatures and pressures. For the sake of simplicity the low-pressure stage has been considered together as a single unit and the following table has been confined to the data of the inlet flow 11 and the outlet flows 19 and 20.

No $NH_3$ was supplied to the washing column 30. The amount of heat discharged via the cooling elements 33 amounted to $3.0 \times 10^6$ kcal/h.

| Flow No. Component | Material flows (in kg/h) | | | | | | | | | | | | |
|---|---|---|---|---|---|---|---|---|---|---|---|---|---|
| | 6 | 7 | 8 | 11 | 19 | 20 | 23 | 24 | 25 | 26 | 28 | 31 | 34 |
| $NH_3$ | 60,250 | 15,445 | | 7,870 | 760 | 7,110 | 930 | 44,251 | 36,640 | 7,575 | 23,610 | 8,040 | 170 |
| $CO_2$ | 38,695 | 17,260 | 30,555 | 9,260 | 305 | 8,955 | 485 | 46,695 | 38,695 | 8,000 | | 9,440 | 180 |
| Urea | | | | 41,665 | 41,665 | | | | | | | | |
| $H_2O$ | 2,515 | 9,930 | | 21,910 | 18,110 | 3,800 | 5,610 | 3,035 | 2,515 | 520 | | 9,410 | |
| Inert | 1,280 | | 265 | | | | | 1,545 | 1,280 | 265 | | | 265 |
| Total | 102,740 | 42,635 | 30,820 | 80,705 | 60,840 | 19,865 | 7,025 | 95,490 | 79,130 | 16,360 | 23,610 | 26,890 | 615 |
| Temp. °C. | 197 | 172 | 75 | 180 | 135 | 115 | 70 | 220 | 220 | 220 | 40 | 77 | 172 |
| Pressure | | | | | | | | | | | | | |

-continued

| Flow No.<br>Component | Material flows (in kg/h) | | | | | | | | | | | |
|---|---|---|---|---|---|---|---|---|---|---|---|---|
| | 6 | 7 | 8 | 11 | 19 | 20 | 23 | 24 | 25 | 26 | 28 | 31 | 34 |
| $kg/cm^2$ | 320 | 320 | 320 | 320 | 3 | 3 | 3 | 320 | 320 | 320 | 370 | 320 | 320 |

What is claimed is:

1. In a process for synthesizing urea from the reaction of ammonia with gaseous carbon dioxide under a pressure in the range of 100–300 atmospheres and at a temperature of 140° to 200°C to form a urea synthesis solution which contains urea, water and ammonium carbamate in a urea synthesis reaction zone and thereafter decomposing the ammonium carbamate in a decomposing and stripping zone, including flowing the urea synthesis solution from the synthesis reaction zone down through a stripping zone, contacting the downward flowing urea synthesis solution with an upward flowing countercurrent stream of at least one gaseous stripping agent selected from the group consisting of $CO_2$, $NH_3$ and inert gas causing the decomposition of the ammonium carbamate and to strip $CO_2$ and $NH_3$ gas released by carbamate decomposition, providing the heat required for the decomposition of ammonium carbamate contained in the urea synthesis solution and for the expelling of gaseous ammonia and carbon dioxide from said solution by transferring most of the heat evolved in the synthesis reaction zon to the urea synthesis solution flowing down through said stripping zone, through a wall separating the urea synthesis reaction zone and the stripping zone, thereby controlling the temperature in the synthesis reaction zone, the decomposition and stripping zone maintained at essentially the same pressure as the synthesis reaction zone, and recycling at least portion of the gas mixture from said decomposing and stripping operation into said urea synthesis reaction zone; the improvement comprising a. maintaining the temperature in the synthesis reaction zone in the range of from about 210° to about 245°C;

b. maintaining the synthesis reaction zone at a pressure of about 250 to 600 atmospheres;

c. conducting the synthesis reaction with a gross molar $NH_3/CO_2$ ratio in the liquid phase between about 2.5 and about 8 so that not all of the gaseous carbon dioxide is reacted; and d. introducing into the bottom part of the urea synthesis reaction zone the portion of the gas mixture to be recycled.

2. The process according to claim 1 wherein the reaction synthesis zone is maintained at a temperature of about 215° to about 230° C.

3. The process according to claim 1 wherein a gas mixture comprising unconverted ammonia, unconverted carbon dioxide and inert gases is discharged at the top of the reaction synthesis zone and that a quantity thereof, corresponding with 10 to 50 percent by weight of the quantity of gas mixture discharged from the stripping zone, is reintroduced to the bottom of the reaction synthesis zone.

4. The process according to claim 3 wherein the recycled gas is directed into the reaction synthesis zone by an ejector driven by ammonia, carbon dioxide or a solution containing ammonium carbamate.

5. The process according to claim 3 wherein the quantity of recycled gas mixture is selected so as to control the temperature or the composition of the stripped synthesis solution.

6. The process according to claim 3 wherein those portions of the gas mixtures discharged from the reaction zone and the stripping zone which have not been recycled are directed into a washing zone wherein ammonia and carbon dioxide are absorbed in a liquid thereby discharging a quantity of heat to control the temperature or the composition of the stripped synthesis solution.

* * * * *